United States Patent
Sukhomlinova et al.

(10) Patent No.: US 8,697,890 B2
(45) Date of Patent: Apr. 15, 2014

(54) DICHROIC-PHOTOCHROMIC 2H-NAPHTHO[1,2-B]PYRAN COMPOUNDS AND DEVICES

(75) Inventors: Ludmila Sukhomlinova, Kent, OH (US); Linli Su, Stow, OH (US); Tamas Kosa, Hudson, OH (US); Bahman Taheri, Shaker Heights, OH (US)

(73) Assignee: Alphamicron Incorporated, Kent, OH (US)

( * ) Notice: Subject to any disclaimer, the term of this patent is extended or adjusted under 35 U.S.C. 154(b) by 741 days.

(21) Appl. No.: 12/446,059

(22) PCT Filed: Oct. 17, 2007

(86) PCT No.: PCT/US2007/022170
§ 371 (c)(1),
(2), (4) Date: Apr. 17, 2009

(87) PCT Pub. No.: WO2008/051420
PCT Pub. Date: May 2, 2008

(65) Prior Publication Data
US 2010/0324296 A1   Dec. 23, 2010

Related U.S. Application Data

(60) Provisional application No. 60/853,383, filed on Oct. 20, 2006.

(51) Int. Cl.
*C07D 311/92* (2006.01)
*G02B 1/04* (2006.01)

(52) U.S. Cl.
USPC ............ 549/389; 252/586; 548/525; 546/196

(58) Field of Classification Search
USPC ............ 252/586; 546/196; 548/525; 549/389
See application file for complete search history.

(56) References Cited

U.S. PATENT DOCUMENTS

| | | | |
|---|---|---|---|
| 5,458,814 A | 10/1995 | Kumar et al. | 252/586 |
| 5,543,533 A | 8/1996 | Allegrini et al. | 549/389 |
| 5,573,712 A | 11/1996 | Kumar et al. | 252/586 |
| 5,623,005 A | 4/1997 | Rickwood et al. | 524/96 |
| 5,650,098 A | 7/1997 | Kumar et al. | 252/586 |
| 5,952,515 A | 9/1999 | Melzig et al. | 549/389 |
| 6,197,225 B1 | 3/2001 | Tanizawa et al. | 252/586 |
| 6,353,102 B1 | 3/2002 | Kumar | 544/60 |
| 6,387,512 B1 | 5/2002 | Clarke et al. | 428/426 |
| 6,630,597 B1 | 10/2003 | Lin et al. | 549/389 |
| 6,690,495 B1 | 2/2004 | Kosa et al. | 359/86 |
| 7,521,004 B2 * | 4/2009 | Momoda et al. | 252/582 |
| 2005/0004361 A1 * | 1/2005 | Kumar et al. | 544/71 |
| 2006/0006336 A1 | 1/2006 | Cano et al. | 250/345 |
| 2008/0088044 A1 | 4/2008 | Cano et al. | 264/1.32 |

FOREIGN PATENT DOCUMENTS

| | | |
|---|---|---|
| EP | 629620 A1 | 12/1994 |
| EP | 0926146 | 6/1999 |
| EP | 1674460 | 6/2006 |
| JP | 08-295690 | * 11/1996 |
| WO | WO 97/21698 | 6/1997 |
| WO | WO 98/04937 | 2/1998 |
| WO | WO 03/080595 A1 | 10/2003 |
| WO | WO 2006/067309 | 6/2006 |

OTHER PUBLICATIONS

Boger—Synthesis, Chemical Properties, and Preliminary Evaluation of Substituted CBI Analogs of CC-1065 and the Duocarmycins Incorporating the 7-Cyano-1,2,9,9a-tetrahydrocyclopropal[c]benz[e]indol-4-one Alkylation Subunit: Hammett Quantitation of the Magnitude of Electronic Effects on Functional Reactivity, Journal of Organic Chemistry, 1996, 61, 4894-4912; the year of publication is sufficiently earlier than the effective filing date so that the particular month of publication is not an issue.

Friedman—The synthesis and transition temperatures of 5-(4-alkyl- and 4-alkoxy-phenyl)-2-cyanobenzo[b]furans and a 5-(4'-alkylbiphenyl-4-yl)-2-cyanobenzo[b]furan: a comparison with their biphenyl and terphenyl analogues; Liquid Crystals 2001; vol. 28, No. 6, 901-912, the year of publication is sufficiently earlier than the effective filing date so that the particular month of publication is not an issue.

Gabbutt—Synthesis and spectroscopic properties of some merocyanine dyes; Elsevier Science Ltd.; Dyes and Pigments 49 (2001) 65-74; the year of publication is sufficiently earlier than the effective filing date so that the particular month of publication is not an issue.

Van Gemert—Benzo and naphthopyrans (Chromenes); Organic Photochromic and Thermochromic Compounds; vol. 1, 1999; the year of publication is sufficiently earlier than the effective filing date so that the particular month of publication is not an issue.

Gabbutt—Synthesis and photochromic properties of substituted 3H-naphtho[2,1-b]pyrans; www.sciencedirect.com; Tetrahedron 61 (2005) 463-471; the year of publication is sufficiently earlier than the effective filing date so that the particular month of publication is not an issue.

Hepworth—Photochromic naphthopyrans; Functional Dyes; Ed. S. IL Kim, Elsevier, Amsterdam, Apr. 2006; 85-135.

Bahadur, et al.—Liquid Crystals: Applications and Uses, vol. 3; "order parameter and dichroic ratio of dyes"; (1992) 99-103, Section 11.4.1; the year of publication is sufficiently earlier than the effective filing date so that the particular month of publication is not an issue.

Baron, et al.—Definition of Basic Terms Relating to Low-Molar-Mass and Polymer Liquid Crystals; Pure Appl. Chem; 2001, 845-895, vol. 73 No. 5; the year of publication is sufficiently earlier than the effective filing date so that the particular month of publication is not an issue.

International Search Report and Written Opinion for International Patent No. PCT/US2007/022170 dated Dec. 1, 2008.

\* cited by examiner

*Primary Examiner* — Noble Jarrell
*Assistant Examiner* — Valerie Rodriguez-Garcia
(74) *Attorney, Agent, or Firm* — Renner Kenner Greive Bobak Taylor & Weber

(57) ABSTRACT

A naphthopyran compound represented by the formula

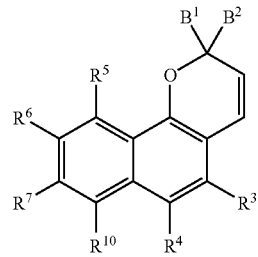

$B^1$ and $B^2$ are selected from a phenyl, naphthyl, or heterocyclic aromatic group, or may combine to form one or more aromatic rings. $B^1$ and $B^2$ are optionally substituted with one or more substituents. $R^3$, $R^4$, $R^5$, $R^6$, and $R^{10}$ are selected independently from hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$. Any two or more of $R^5$, $R^6$ or $R^{10}$ may combine to form a cyclic group. $R^7$ is a mesogenic group containing at least two rings connected to each other through a covalent bond or linking unit. The linking unit is an ester, —$R^d$—, —O—, —$OR^d$—, —$OR^dO$—, —$OCOR^d$—, —$OCOR^dO$—, —S—, —CH=CH—, —CH=N—, —C≡C—, or —N=N—, where $R^d$ is a linear or branched ($C_{1-18}$)alkyl or a linear or branched ($C_{1-18}$)haloalkyl group. The naphthopyran compound may be incorporated into an optical article.

19 Claims, 1 Drawing Sheet

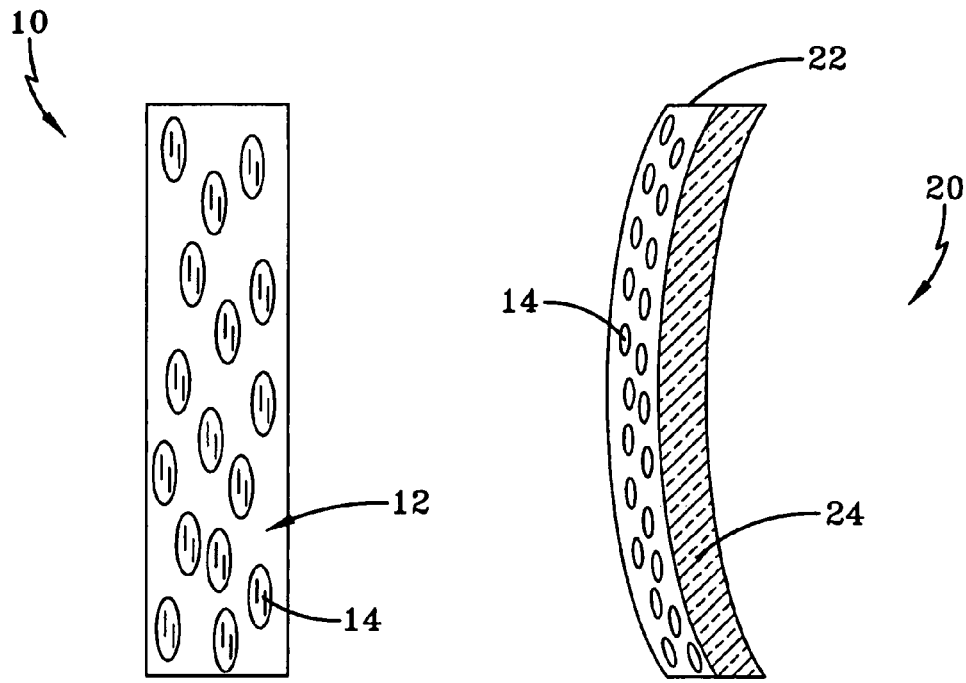
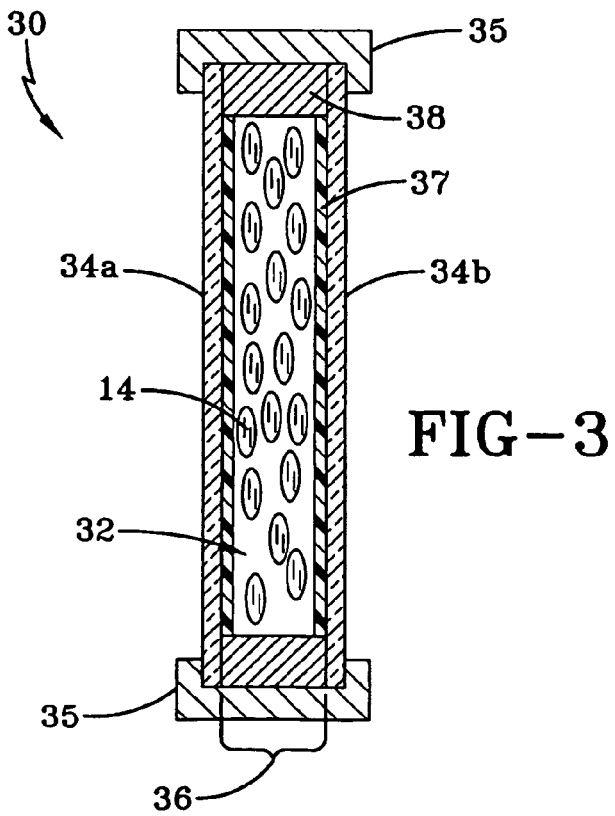

DICHROIC-PHOTOCHROMIC 2H-NAPHTHO[1,2-B]PYRAN COMPOUNDS AND DEVICES

CROSS-REFERENCE TO RELATED APPLICATIONS

This application claims priority of U.S. Provisional Application Ser. No. 60/853,383 filed Oct. 20, 2006 which is incorporated herein by reference.

TECHNICAL FIELD

The present invention is directed to a group of novel compounds that exhibit both photochromic and dichroic properties and their use in optical articles, especially in optical lenses such as ophthalmic lenses.

BACKGROUND ART

Photochromism is a well known physical phenomenon that is observed with certain classes of chemical compounds. A detailed discussion of this phenomenon can be found in "Photochromism: Molecules and Systems", Studies in Organic Chemistry 40, edited by H. Durr and H. Bouas-Laurent, Elsevier, 1990.

A number of substituted 2H-naphtho[1,2-b]pyrans are known to be capable of exerting a reversible photochromic effect, as described for example in International Patent Application Nos. WO 95/16215 and WO 00/18755, and U.S. Pat. Nos. 6,387,512 and 6,353,102. However, none of these 2H-naphtho[1,2-b]pyrans compounds are reported to have dichroic properties.

Passive photochromic devices, i.e. devices containing photochromic dyes whose absorbance depends only from the presence or absence of UV light, typically exhibit rather quick activation (coloration) but it generally takes several minutes or even tens of minutes to revert from the colored to the bleached state. This slow fading is a severe drawback for the user of photochromic glasses who has to them take off to have clear vision when leaving the sunlight and entering dimmer light conditions.

Therefore, there is a need for compounds exhibiting not only good photochromic properties, such as high absorption in the colored state, fast coloring and fading rates, but which also are capable of dichroism and light polarization when in a spatially ordered condition, for example when incorporated into liquid crystals or oriented polymer host materials.

SUMMARY OF THE INVENTION

In light of the foregoing, it is a first aspect of the present invention to provide photochromic compounds and devices which incorporate those compounds.

It is another aspect of the present invention to provide a naphthopyran compound represented by the formula I

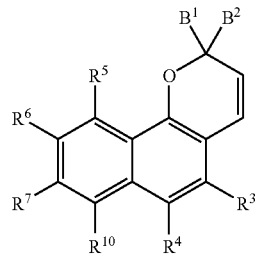

wherein $B^1$ and $B^2$ may independently include (i) a phenyl group, (ii) a naphthyl group, (iii) a heterocyclic aromatic group, (iv) a combination thereof, or wherein $B^1$ and $B^2$ may combine to form one or more aromatic rings; wherein $B^1$ and $B^2$ may further include one or more substituents selected from the group consisting of halogen, —$R^a$, —OH, —$OR^a$, —SH, —$SR^a$, —$SOR^a$, —$SO_2R^a$, —$NR^aR^a$, —$NR^bR^c$, —CN, —$NO_2$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$) alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group; wherein $R^3$, $R^4$, $R^5$, $R^6$, and $R^{10}$ are selected independently from the group consisting of hydrogen, halogen, —$R^a$, —OH, —$OR^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^3$, $R^4$, $R^5$, $R^6$, and $R^{10}$ combine to form a cyclic group, and wherein $R^7$ is a mesogenic group.

It is also an aspect of the present invention to provide a naphthopyran compound represented by the formula II

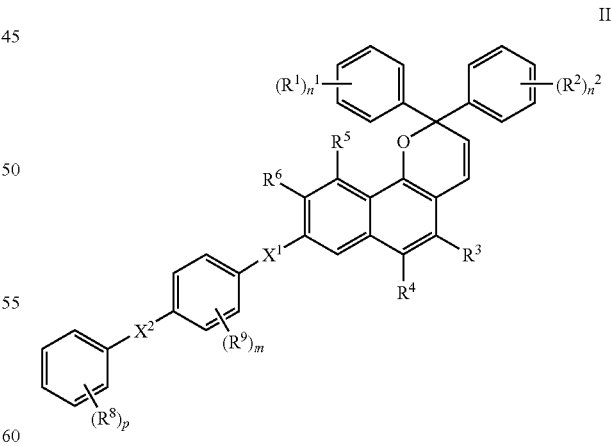

wherein $R^1$, $R^2$, and $R^8$, are selected independently from the group consisting of hydrogen, halogen, —$R^a$, —OH, —SH, —$SR^a$, —$NH_2$, —$NR^bR^c$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched (C$_{1-20}$) haloalkyl, perhaloalkyl group, linear or branched (C$_{1-20}$) alkynyl, linear or branched (C$_{1-20}$) polyalkynyl, linear or branched (C$_{1-20}$) hydroxyalkynyl, linear or branched (C$_{1-20}$) polyhydroxyalkynyl; R$^b$ and R$^c$ are independently selected from the group consisting of hydrogen and linear or branched (C$_{1-20}$)alkyl groups, or wherein R$^b$ and R$^c$ combine to form a saturated 5- to 7-member heterocyclic group, or wherein R$^b$ and R$^c$ together and in combination with an adjacent phenyl group form a julolidinyl group, n$^1$ is an integer from 0 to 5,
n$^2$ is an integer from 0 to 5,
p is an integer from 0 to 5,
m is an integer from 0 to 4, each R$^3$, R$^4$, R$^5$, R$^6$, and R$^9$ are selected independently from the group consisting of hydrogen, halogen, —R$^a$, —OH, —OR$^a$, —CN, —NO$_2$, —SO$_2$R$^a$, —SH, —SR$^a$, —NH$_2$, —NHR$^a$, —NR$^a$R$^a$, and —NR$^b$R$^c$; or wherein any two or more of R$^3$, R$^4$, R$^5$, R$^6$, and R$^9$ combine to form a cyclic group, and wherein X$^1$ and X$^2$, identical or different from each other, are covalent bonds or linking units.

It is a further aspect of the present invention to provide a napthopyran compound represented by the formula III

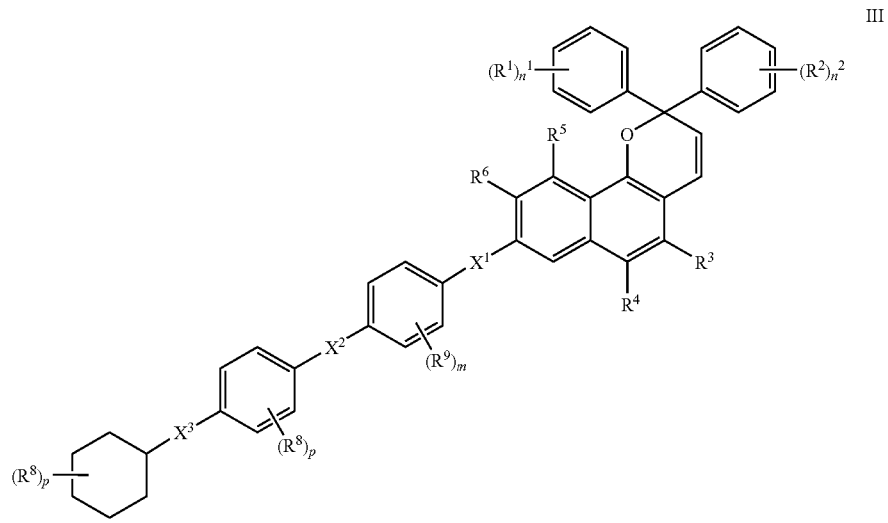

III wherein R$^1$, R$^2$, and R$^8$, are selected independently from the group consisting of hydrogen, halogen, —R$^a$, —OH, —OR$^a$, —SH, —SR$^a$, —NH$_2$, —NR$^b$R$^c$, —CO—R$^a$, —O—CO—R$^a$, and —CO$_2$R$^a$, wherein R$^a$ is a linear or branched (C$_{1-20}$) alkyl, (C$_{3-20}$) cycloalkyl, (C$_{4-20}$) polycycloalkyl linear or branched (C$_{1-20}$) alkenyl, linear or branched (C$_{1-20}$) polyalkenyl, linear or branched (C$_{1-20}$) haloalkyl, perhaloalkyl group, linear or branched (C$_{1-20}$) alkynyl, linear or branched (C$_{1-20}$) polyalkynyl, linear or branched (C$_{1-20}$) hydroxyalkynyl, linear or branched (C$_{1-20}$) polyhydroxyalkynyl; R$^b$ and R$^c$ are independently selected from the group consisting of hydrogen and linear or branched (C$_{1-20}$)alkyl groups, or wherein R$^b$ and R$^c$ combine to form a saturated 5- to 7-member heterocyclic group, or wherein R$^b$ and R$^c$ together and in combination with an adjacent phenyl group form a julolidinyl group, n$^1$ is an integer from 0 to 5,
n$^2$ is an integer from 0 to 5,
p is an integer from 0 to 5,
m is an integer from 0 to 4, each R$^3$, R$^4$, R$^5$, R$^6$, and R$^9$ are selected independently from the group consisting of hydrogen, halogen, —R$^a$, —OH, —OR$^a$, —O—CO—R$^a$, —CN, —NO$_2$, —SO$_2$R$^a$, —SOR$^a$, —SH, —SR$^a$, —NH$_2$, —NHR$^a$, —NR$^a$R$^a$, and —NR$^b$R$^c$; or wherein any two or more of R$^3$, R$^4$, R$^5$, R$^6$, and R$^9$ combine to form a cyclic group, and wherein X$^1$, X$^2$ and X$^3$, identical or different from each other, are covalent bonds or linking units.

Yet another aspect of the present invention provides an optical article comprising one or more naphthopyran compounds of the present invention.

BRIEF DESCRIPTION OF THE DRAWINGS

For a complete understanding of the objects, techniques and structure of the invention, reference should be made to the following detailed description and accompanying drawings, wherein:

FIG. 1 is a cross-sectional schematic view of an optical article according to the present invention with naphthopyran compound incorporated into a host material;

FIG. 2 is a cross-sectional schematic view of another optical article according to the present invention with naphthopyran compound incorporated into a surface coating or film applied to an optical substrate; and FIG. 3 is a cross-sectional schematic view of yet another optical article according to the present invention in which naphthopyran compound is carried in a device.

BEST MODE FOR CARRYING OUT THE INVENTION

As used herein, the term "dichroic-photochromic" refers to a dye or compound that exhibits both dichroic and photochromic properties. In other words, a dichroic photochromic material is not simply a combination of photochromic material and a dichroic dye, but a photochromic material that exhibits dichroism. It will further be appreciated that the term dichroic-photochromic includes the naphthopyran compounds to be discussed herein.

The present invention provides dichroic-photochromic 2H-naphtho[1,2-b]pyrans having a mesogenic group at C-8 of the naphthopyran ring. In one or more embodiments, the 2H-naphtho[1,2-b]pyrans may be represented by the formula I

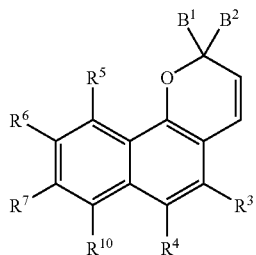

wherein $B^1$ and $B^2$ may independently include (i) a phenyl group, (ii) a naphthyl group, (iii) a heterocyclic aromatic group, (iv) a combination thereof, or wherein $B^1$ and $B^2$ may combine to form one or more aromatic rings; wherein $B^1$ and $B^2$ may further include one or more substituents selected from the group consisting of halogen, —$R^a$, —OH, —$OR^a$, —SH, —$SR^a$, —$SOR^a$, —$SO_2R^a$, —$NR^aR^a$, —$NR^bR^c$, —CN, —$NO_2$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$) alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group; wherein $R^3$, $R^4$, $R^5$, $R^6$, and $R^{10}$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^3$, $R^4$, $R^5$, $R^6$, and $R^{10}$ combine to form a cyclic group, and wherein $R^7$ is a mesogenic group. Examples of ($C_{4-20}$) polycycloalkyl groups include norbornyl and adamantyl. In one or more embodiments, $B^1$ includes a phenyl group and a heterocyclic aromatic group. In these or other embodiments, $B^2$ includes a phenyl group and a heterocyclic aromatic group. In one or more embodiments, $R^b$ and $R^c$ may combine to form a heterocyclic group that includes at least one additional oxygen or nitrogen heteroatom. In one or more embodiments, two or more of $R^3$, $R^4$, $R^5$, $R^6$, and $R^{10}$ combine to form a phenyl group, a cyclic group, a heterocyclic group, or combinations thereof.

Mesogenic groups include rod-like moieties that are structurally compatible with the formation of liquid crystal phases in the molecular system in which they exist. In one or more embodiments, mesogenic groups contain at least two rings connected to each other through a covalent bond or a linking unit. The rings, which may be the same or different, may include 5- or 6-membered aromatic or non-aromatic rings. The rings may be selected independently from benzene, substituted benzene, naphthalene, substituted naphthalene, cyclohexane, substituted cyclohexane, heterocyclic rings and substituted heterocyclic rings. Examples of heterocyclic rings include 5- or 6-membered rings and may include one or more members selected from nitrogen, oxygen, and sulfur. In one or more embodiments, the ring that is closest to the naphthopyran group is aromatic, and is linked to the naphthopyran group via a linking group or covalent bond.

Examples of mesogenic groups include groups that may be represented by the following formulas:

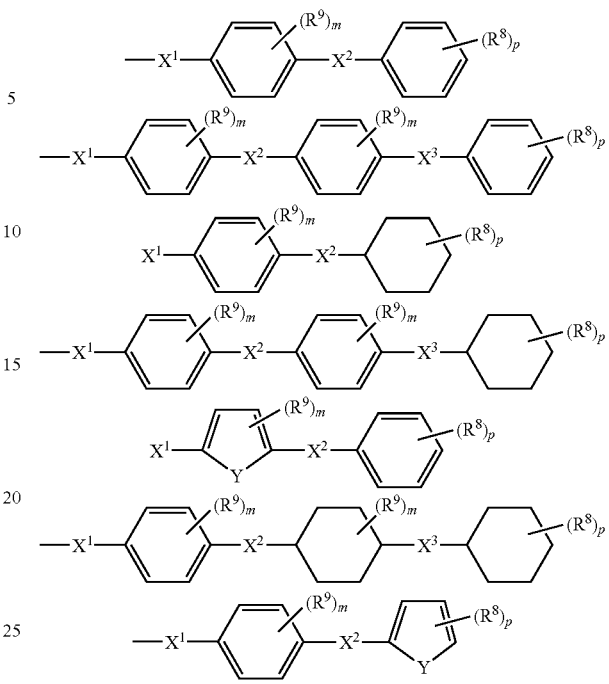

wherein $R^8$, $R^9$, m, p are as described hereinabove, wherein $X^1$, $X^2$, and $X^3$, identical or different from each other, are covalent bonds or linking units, and wherein Y is oxygen, nitrogen, or sulfur. Linking units include divalent organic groups. Examples of linking units include alkyl, ether, ester, ethylene, acetylene, imino, azo, and thio groups. Linking units include groups that may be represented by the formulas —$R^d$—, —O—, —$OR^d$—, —$OR^dO$—, —OCO—, —$OCOR^d$—, —$OCOR^dO$—, —S—, —CH=CH—, —CH=N—, —C≡C—, or —N=N—, wherein $R^d$ is a linear or branched ($C_{1-18}$)alkyl group or a linear or branched ($C_{1-18}$) haloalkyl group.

In one or more embodiments, incorporation of a mesogenic moiety significantly improves dichroic properties of the photochromic dyes in the activated state. The dye compounds, when incorporated into anisotropic host materials such as liquid crystals or oriented polymers, will strongly align with the host material molecules and exhibit strong dichroism, i.e. light polarizing properties, in the colored state.

The skilled artisan will understand that order parameter measures the degree of directional order of the absorption dipole moment of the dye molecules relative to the director of the host liquid crystal (the direction of interest). An order parameter of one (1) refers to complete order while an order parameter of zero indicates the lack of any order.

In one or more embodiments, the dichroic-photochromic dyes of the present invention present an order parameter of greater than about 0.7 and excellent solubility in liquid crystal hosts and most organic solvents. In other embodiments, the dichroic-photochromic dyes of the present invention present an order parameter of greater than about 0.6, and in yet other embodiments, the dichroic-photochromic dyes of the present invention present an order parameter of greater than about 0.5. One will understand that the order parameter value will depend upon various factors, such as the liquid crystal host.

In certain embodiments, the photochromic dyes of the present invention surprisingly present a very fast fading rate, especially when dissolved in a fluid, mesomorphous or gel host medium. In one or more embodiments, they are able to revert from the colored to the bleached state in less than a minute.

In one or more embodiments, the present invention provides naphthopyran compounds represented by the formula II

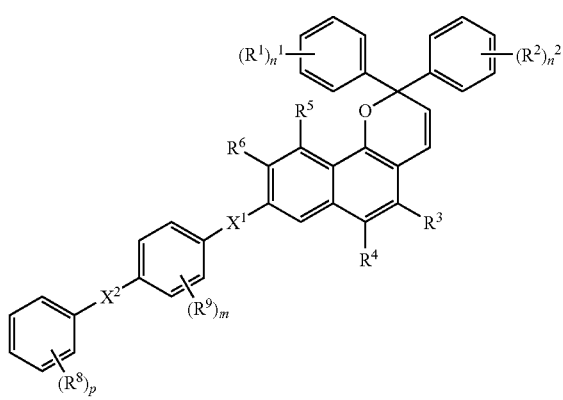

wherein $R^1$, $R^2$, and $R^8$, are selected independently from the group consisting of hydrogen, halogen, —$R^a$, —OH, —$OR^a$, —SH, —$SR^a$, —$NH_2$, —$NR^bR^c$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$)alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group, $n^1$ is an integer from 0 to 5,
$n^2$ is an integer from 0 to 5,
p is an integer from 0 to 5,
m is an integer from 0 to 4, each $R^3$, $R^4$, $R^5$, $R^6$, and $R^9$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^3$, $R^4$, $R^5$, $R^6$, and $R^9$ combine to form a cyclic group, and wherein $X^1$ and $X^2$, identical or different from each other, are covalent bonds or linking units.

Examples of compounds of formula II include compounds represented by the following formulas (a) to (j):

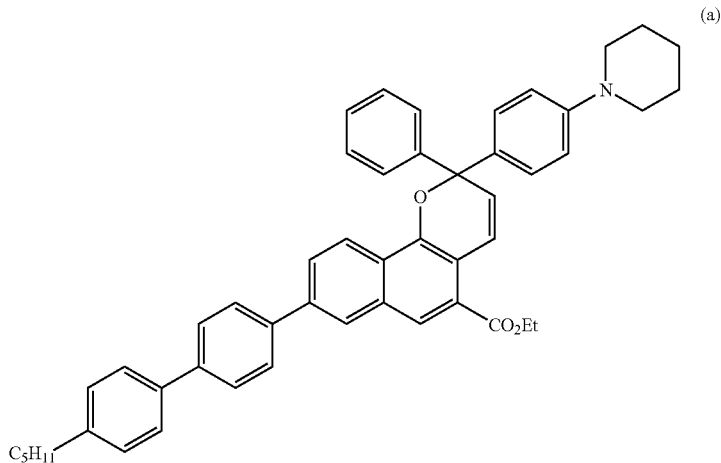

(a)

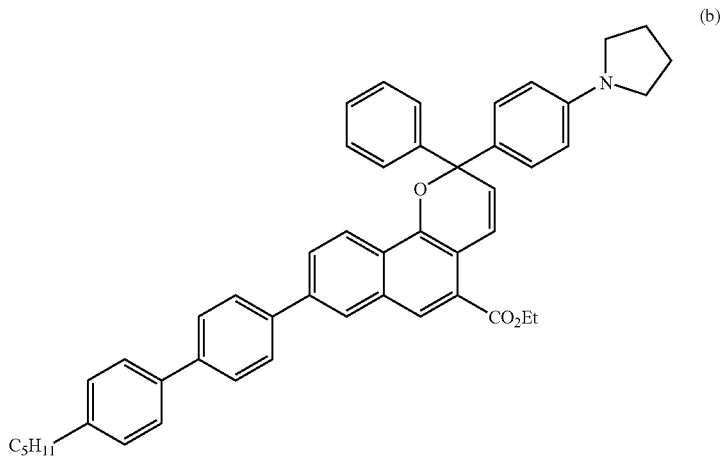

(b)

-continued
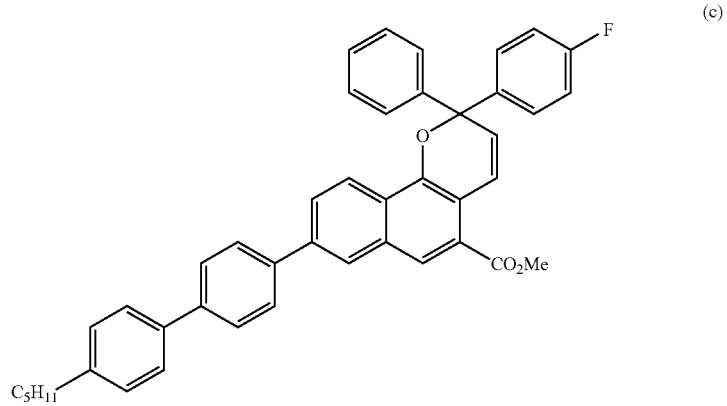
(c)
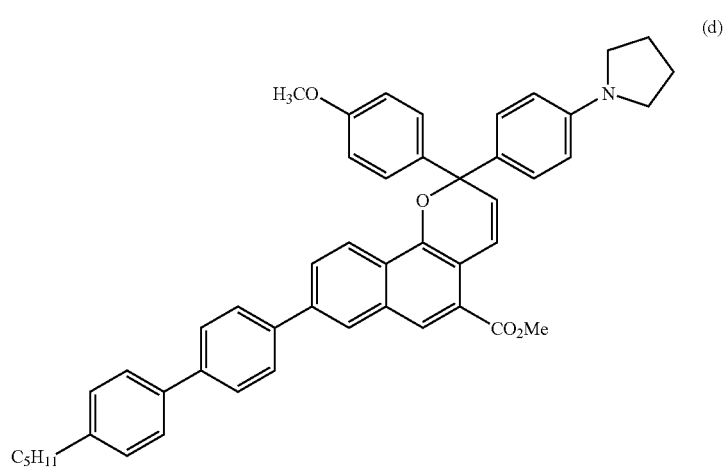
(d)
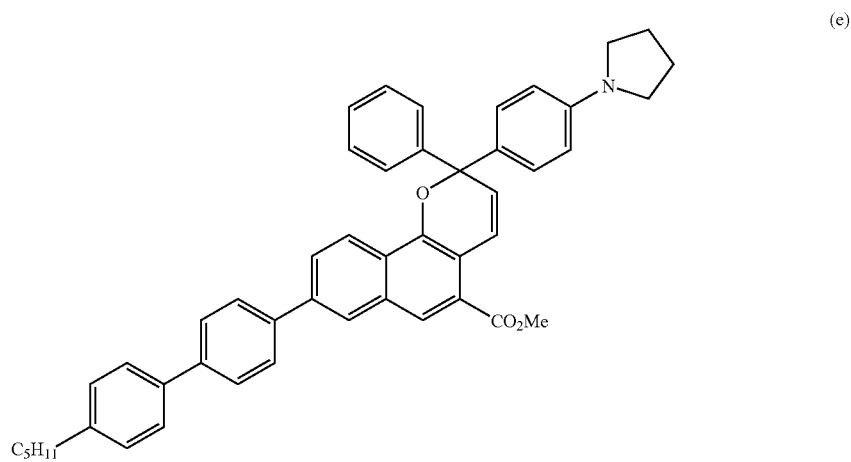
(e)

-continued
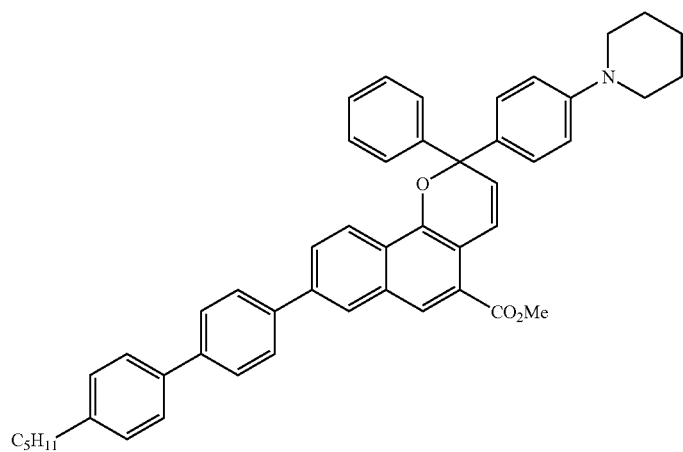
(f)
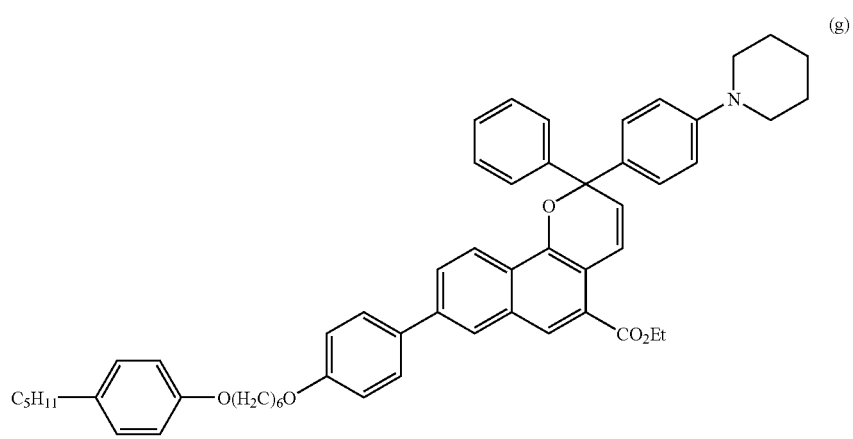
(g)
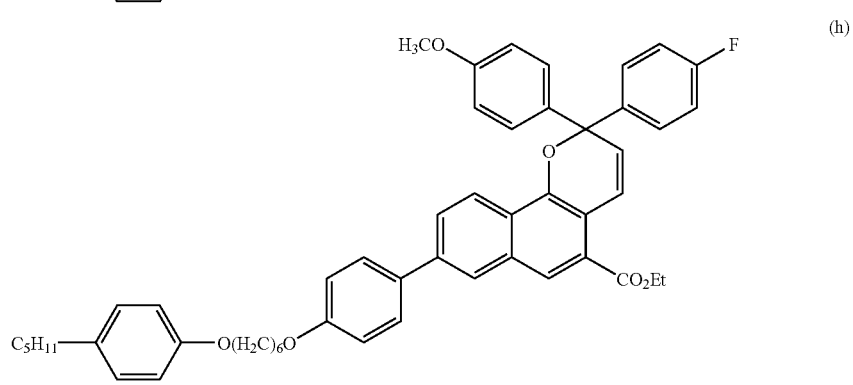
(h)
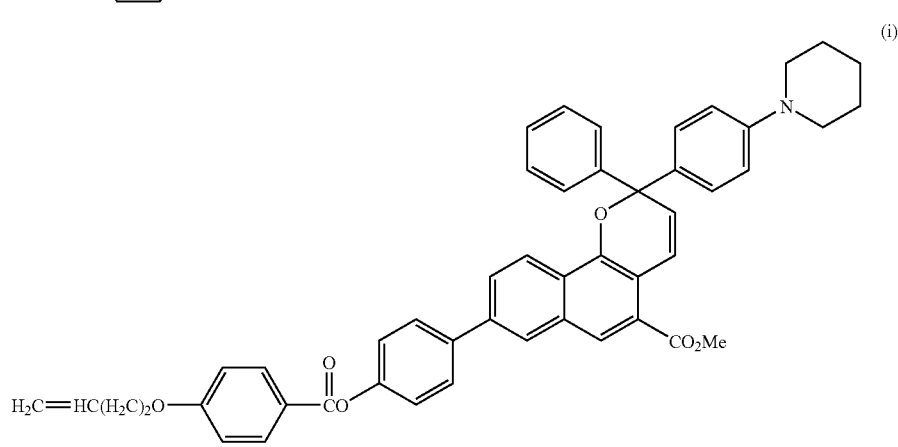
(i)

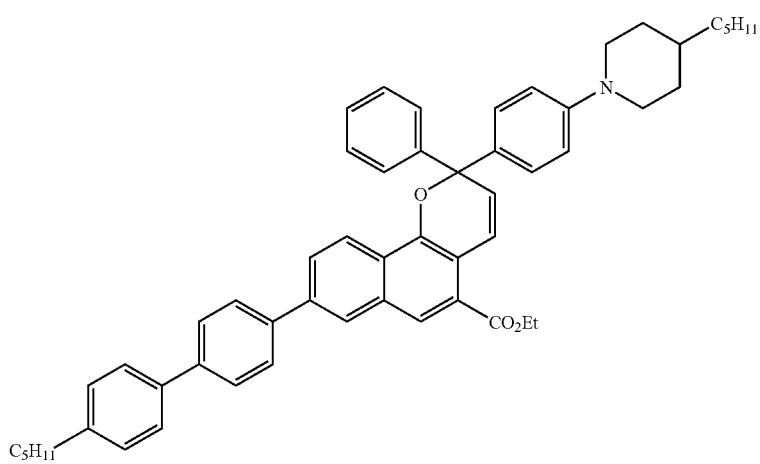

Compounds represented by formula II may be prepared according to the following reaction schemes:

Scheme 2 has been described in the scientific literature, for example, in C. D. Gabbutt, J. D. Hepworth, B. M. Heron, S. M. Partington, D. A. Thomas, *Dye and Pigments,* 2001, 49, 65, which is hereby incorporated by reference.

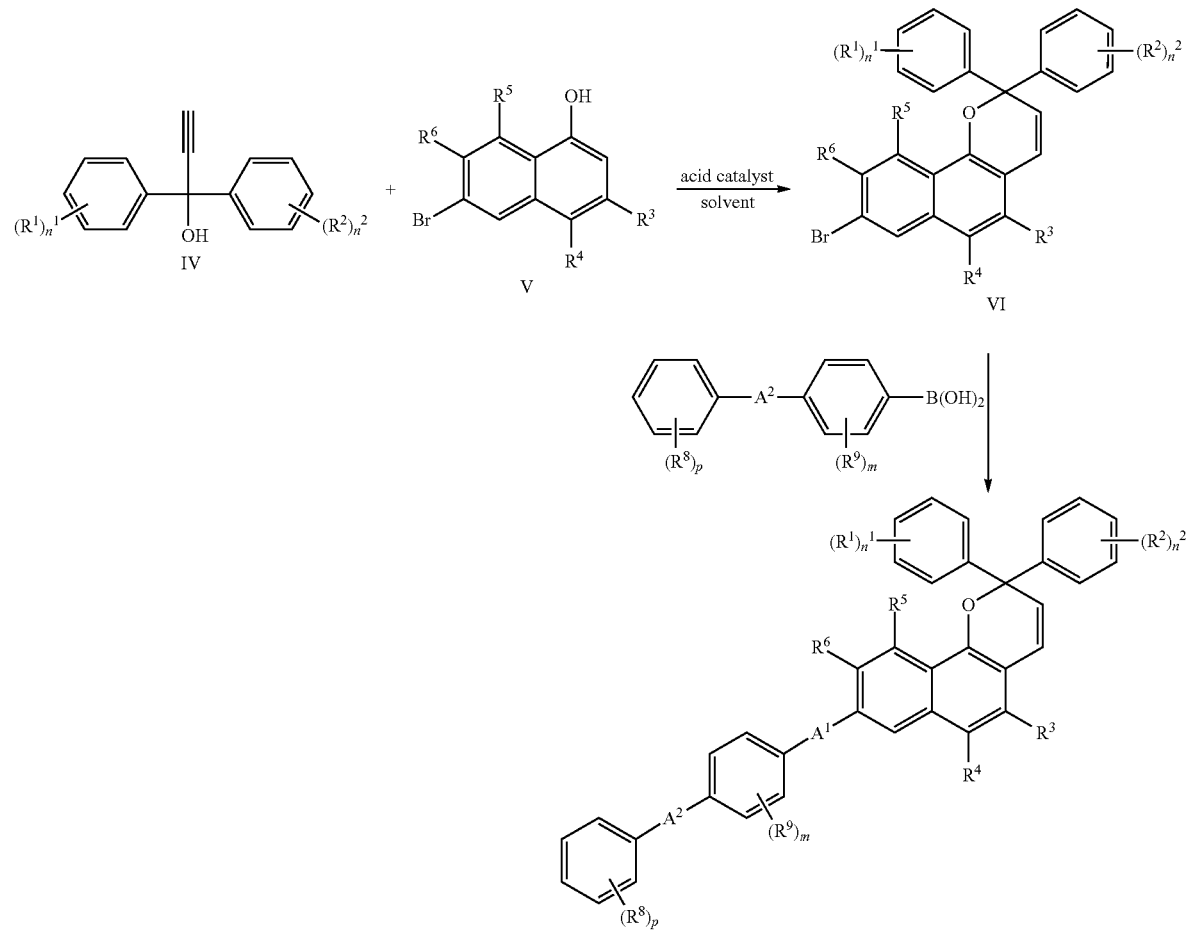

The synthesis of 1,1-diarylprop-2-yn-ols (IV) from lithium trimethylsilylacetylide and benzophenone according to the The requisite naphthols (V) may be prepared, as shown, for example, for ethyl 7-bromo-4-hydroxy-2-naphthalenecarboxylate (Va) in Scheme 3, by Stobbe condensation of 3-bromobenzaldehyde with dialkyl succinate, followed by intramolecular acylation and removal of acetyl group by base hydrolysis according to the published procedure (D. L. Boger, N. Han, C. M. Tarby, C. W. Boyce, H. Cai, Q. Jin, P. Kitos, *J. Org. Chem.*, 1996, 61, 4894, which is hereby incorporated by reference).

The preparation of the 8-bromo-naphtho[1,2-b]pyrans (VI) may be accomplished by the acid catalyzed condensation of the appropriate naphthols (V) and alkynol derivatives (IV) as shown in Scheme 1. This route to naphthopyrans has been reviewed (B. Van Gemert, *Organic Photochromic and Thermochromic Compounds Volume* 1: *Main Photochromic Families*, Ed. J. C. Crano and R. Gugglielmetti, Plenum Press, New York, 1998, p. 111; J. D. Hepworth and B. M. Heron, *Functional Dyes*, Ed. S.-H. Kim, Elsevier, Amsterdam, 2006, p. 85; C. D. Gabbutt, B. M. Heron, A. C. Instone, P. R. Horton, M. B. Hursthouse, *Tetrahedron*, 2005, 61, p. 463, all of which are hereby incorporated by reference).

The 8-bromo-naphtho[1,2-b]pyrans (VI) may serve as substrates for further modification by Suzuki coupling with appropriate substituted phenylboronic acid (prepared as described by e.g. M. R. Friedman, K. J. Toyne, J. W. Goodby and M. Hird, *Liquid Crystals*, 2001, 28, 901, hereby incorporated by reference) to give the 8-substituted naphtho[1,2-b]pyrans of general structure (II) as illustrated by examples (a)-(i).

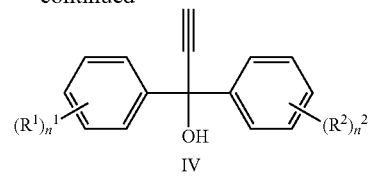

In one or more embodiments, the present invention provides naphthopyran compounds represented by the formula III wherein $R^1$, $R^2$, and $R^8$, are selected independently from the group consisting of hydrogen, halogen, —$R^a$, —OH, —$OR^a$, —SH, —$SR^a$, —$NH_2$, —$NR^bR^c$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$)alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group, $n^1$ is an integer from 0 to 5, $n^2$ is an integer from 0 to 5, p is an integer from 0 to 5, m is an integer from 0 to 4, each $R^3$, $R^4$, $R^5$, $R^6$, and $R^9$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^3$, $R^4$, $R^5$, $R^6$, and $R^9$ combine to form a cyclic group, and wherein $X^1$, $X^2$ and $X^3$, identical or different from each other, are covalent bonds or linking units.

Examples of compounds of formula III include compounds represented by the following formulas (k) to (l):

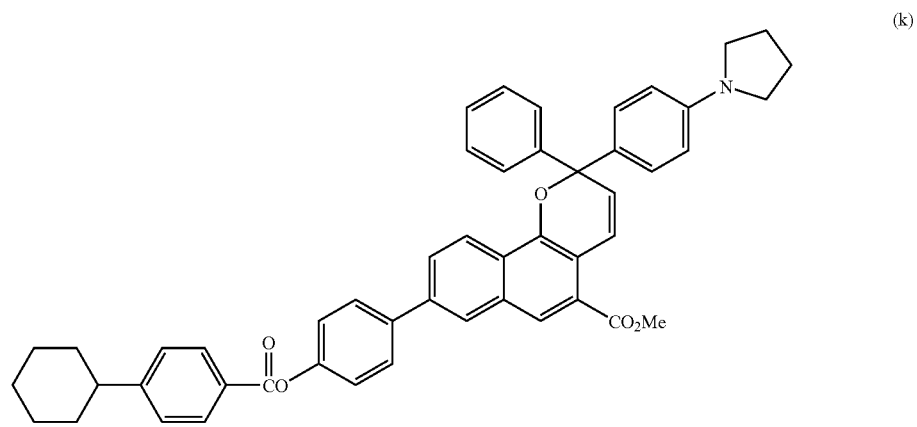

(k)

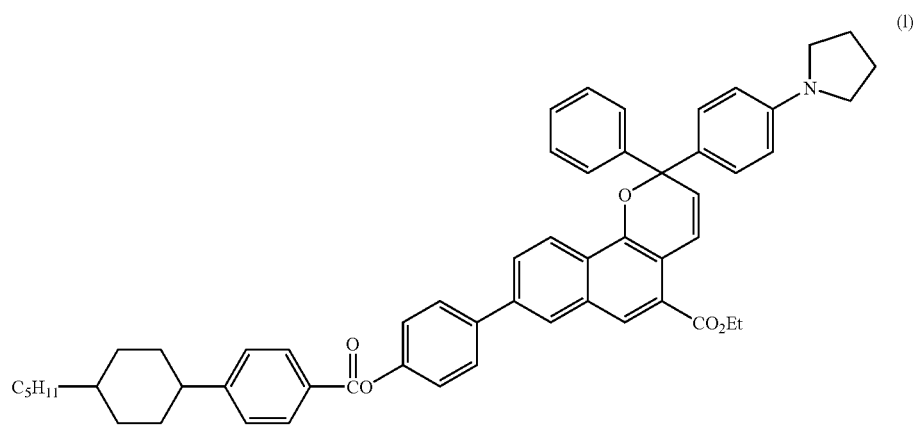

(l)

Compound represented by formula IIIk may be prepared according to the following reaction schemes (Example 11):

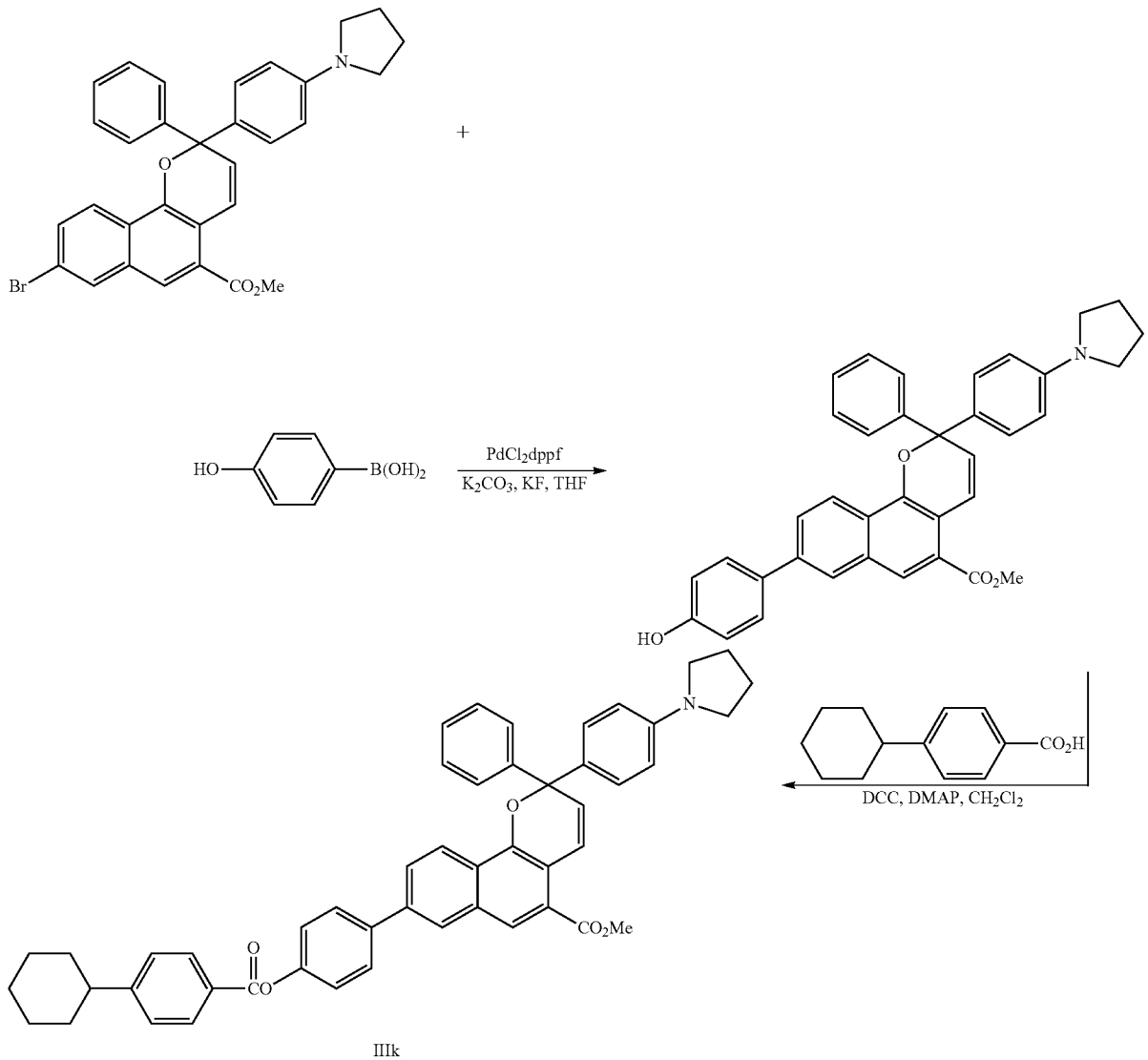

Scheme 4

The present invention also provides an optical article comprising one or more naphthopyran compounds of the present invention. The naphthopyran compounds of the present invention can be used in all kinds of optical devices and elements, such as ophthalmic elements and devices, display elements and devices, windows or mirrors. Non-limiting examples of ophthalmic elements include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive and aircraft windows, building windows in roofs, ceilings, doors, and walls, and optical filters, shutters, and switches.

In one or more embodiments, the optical article of the present invention is a lens, and in certain embodiments, an ophthalmic lens.

In one embodiment, as seen in FIG. 1, the naphthopyran compounds may be incorporated into the bulk of a polymeric material of an optical article designated generally by the numeral 10. Such a polymeric host material may be generally a solid transparent or optically clear material designated generally by the numeral 12. Examples of polymeric host materials include polymers of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly (vinyl acetate), poly(vinyl alcohol), polyurethanes, polycarbonates, poly(ethylene terephtalate), polystyrene, polyfluorostyrene, poly(diethylene glycol bis(alkyl carbonate)), and mixtures thereof.

Dichroic-photochromic compounds 14, which also referred to above as naphthopyran compounds, of the present invention may be incorporated into the polymeric host material 12 by various methods described in the art. The dichroic-photochromic compound or dye may be dissolved or dispersed within the host material. The dichroic-photochromic compound or dye may be added to the monomeric host material prior to polymerization, or by imbibition of the dichroic-photochromic compound into the host material by immersion of the host material in a heated solution of the dichroic-photochromic compound.

In another embodiment of an optical article designated by the numeral 20 according to the present invention and as best seen in FIG. 2, the dichroic-photochromic compound 14 may be incorporated into a surface coating or a film 22 applied to an optical substrate 24. The substrate 24 may include a transparent or optically clear material, such as glass or organic polymers commonly used in optical applications and may be flat or curved and of any shape.

In one or more embodiments, the optical article includes a naphthopyran compound of the present invention incorporated both into the bulk and into the coating of the article. In other words, the optical substrate 24 could be in the form of the optical article 10 described above.

In one or more embodiments of the present invention, the coating or film 22 includes an anisotropic film or coating, i.e. it comprises a layer or medium that is able to function as an alignment layer for dye molecules. Such an alignment layer may be for example an organic polymer, such as polyvinyl alcohol (PVA). One common method of aligning the molecules of a dichroic-photochromic dye, as described above, involves heating a sheet or layer of PVA to soften the PVA and then stretching the sheet to orient the polymer chains. The dichroic-photochromic dye is then impregnated into the stretched sheet and dye molecules take the orientation of the polymer chains. Alternatively, the dye can be first impregnated into the PVA sheet, and thereafter the sheet can be heated and stretched as described above to orient the PVA polymer chains and associated dyes. In this manner, the molecules of the dye can be suitably positioned or arranged within the oriented polymer chains of the PVA sheet.

In one or more embodiments of the present invention, the novel naphthopyran compounds may be incorporated into a fluid, mesomorphous, or gel host medium. The naphthopyran may be dissolved or dispersed in the host medium.

In certain embodiments, dissolving or dispersing a naphthopyran compound of the present invention into a fluid, mesomorphous, or gel host medium increases the coloration rate and even more drastically the fading rate. In one embodiment, the recovery time, i.e. the time it takes the material to revert from an absorptive condition to a clear condition, is reduced to less than about 20 seconds, in another embodiment to less than about 15 seconds, in yet another embodiment to less than about 10 seconds, in still yet another embodiment to less than about 5 seconds, and in another embodiment to less than or equal to about 2 seconds.

The fluid, mesomorphous, or gel host medium incorporating the at least one naphthopyran compound may include organic solvents, liquid crystals, polymers, or mixtures thereof.

Examples of organic solvents include benzene, toluene, methyl ethyl ketone, acetone, ethanol, tetrahydrofurfuryl alcohol, N-methylpyrrolidone, 2-methoxyethyl ether, xylene, cyclohexane, 3-methyl cyclohexanone, ethyl acetate, tetrahydrofuran, methanol, methyl propionate, ethylene glycol and mixtures thereof.

Examples of liquid crystals include nematic, chiral nematic, and polymeric liquid crystals. In one or more embodiments, liquid crystals may be used in combination with an organic solvent, for example one of the organic solvents mentioned above.

Examples of polymers include elastomers and adhesives. In one or more embodiments, polymers may be used in combination with liquid crystals, for example one of the liquid crystal types mentioned above, and an organic solvent, for example one of the organic solvents mentioned above.

In one or more embodiments, as seen in FIG. 3, an optical article is designated generally by the numeral 30. The article 30 comprises a mixture, designated generally by the numeral 32, of a fluid, mesomorphous, or gel host medium and at least one of the naphthopyran compounds 14 of the present invention may be incorporated into the mixture, wherein a mechanism holds the mixture in a mechanically stable environment.

In one or more embodiments, the article 30 includes a pair of opposed substrates 34 *a,b* having a gap therebetween for receiving the mixture of a fluid, mesomorphous or gel host medium and at least one dichroic-photochromic dye of the present invention, and optionally a frame 35 for carrying the pair of substrates. The substrates 34*a,b* are separated by spacers or the like so as to form a gap 36 therebetween. Depending upon the end-use application and design considerations, the gap 36 may be between about 3 to 150 microns, and ideally between about 10 to 100 microns. Alignment layers 37, which may assist in orienting the dichroic-photochromic compound 14, may be positioned on the facing surfaces of the substrates. A sealing material, such as an optical adhesive 38 may be used to contain the mixture 32 between the substrates. It will further be appreciated that electrode layers may be provided on the substrates to allow for application of an electric field across the gap and provide another way to control the properties of the liquid crystal material. This type of article is further described in U.S. Pat. No. 6,690,495, which is hereby incorporated by reference.

In one or more embodiments, the article comprises an optical component that includes at least one transparent cell arrangement juxtaposed in a parallel direction to the surface thereof. Such transparent cell arrangements are described in International Patent Application Nos. WO 2006/013250, WO 2006/067309, and French Patent No. 2879757, all of which are hereby incorporated by reference. Each cell may be tightly closed and may contain the mixture of a fluid, mesomorphous, or gel host medium and at least one naphthopyran compound as described hereinabove. In one embodiment, the transparent cell arrangement forms a layer whose height perpendicular to the component surface is less than about 100 microns (μm), in another embodiment less than about 50 μm. In one or more embodiments, the height perpendicular to the component surface is from about μm to about 50 μm.

The transparent cell arrangement may be formed either directly in a transparent rigid substrate of the optical article or optical component as seen in FIG. 1, or alternatively a transparent film 22 incorporating the materials described above may be applied on a surface of a transparent rigid substrate or optical component of the optical article as seen in FIG. 2. The transparent film may also be configured between the facing surfaces of two optical components or substrates.

In one or more embodiments, the film occupies a relatively large fraction of the total surface of the optical component. In one embodiment, the surface occupied by the film is at least about 70% of the total surface of the optical component. In certain embodiments, the surface occupied by the film is from about 90 up to about 100% of the total surface of the optical component.

One or more embodiments of the present invention provides dichroic-photochromic dyes exhibiting good photochromic properties, such as high absorption in the colored state, fast coloring and fading rates, and also exhibiting dichroism and light polarization when in a spatially ordered condition, for example when incorporated into liquid crystals or oriented polymer host materials.

In order to demonstrate the practice of the present invention, the following examples have been prepared and tested. The examples should not, however, be viewed as limiting the scope of the invention. The claims will serve to define the invention.

EXAMPLES

Dichroic-photochromic compounds were prepared as described below for Examples 1-12. Order parameter measurements were made. A 15 micron sandwich type glass cell, containing two identical chambers was used. The two inner facing sides of the cell separated by the spacers were coated with polyimide layer having planar alignment and rubbed in an anti-parallel fashion. One chamber was filled with the liquid crystal host only and used as a reference, and the other chamber was filled with a mixture of a dichroic-photochromic compound dissolved in the liquid crystal host. ZLI-4788-100 (EMD Chemicals Inc., Germany) was used as a liquid crystal host. An Ocean Optics Spectrometer with a Tungsten Halogen lamp as the visible light source for detection was used. A polarizer was placed in front of the light source to generate polarized visible light. Two UV Light Emitting Diodes were used to illuminate the cell with UV light to activate the dichroic-photochromic compound. The dichroic ratio and order parameter were measured for the dichroic-photochromic compound in its UV-activated state. The cell is usually illuminated with UV light for about 5 minutes before each measurement to ensure that the dichroic-photochromic compound has achieved a dynamic equilibrium between the ground state and the activated state.

Example 1

Ethyl 8-(4-pentylbiphenyl)-2-phenyl-2-(4-piperidinophenyl)-2-H-naphtho[1,2-b]pyran-5-carboxylate (IIa) was prepared by the following procedure.

Ethyl 8-bromo-2-phenyl-2-(4-piperidinophenyl)-2-H-naphtho[1,2-b]pyran-5-carboxylate (2.0 g, 3.5 mmol) was dissolved in THF (20 ml) containing water (2 ml) under nitrogen and diphenylphosphinoferrocene palladium dichloride (0.025 g, 1 mol %) was added. The solution was stirred for 5 min and potassium carbonate (0.53, 3.9 mmol), potassium fluoride (0.67 g, 11.6 mmol), and 4-pentylbiphenyl boronic acid (1.04 g, 3.9 mmol) were added. The reaction mixture was refluxed for 20 hours. Solvent was removed and the residue was flash chromatographed using petroleum ether-ethyl acetate (93-7) on silica gel. Recrystallization from ethyl acetate and hexane gave the title compound with melting point (m.p.) 131-132° C. and order parameter (S) 0.735.

Example 2

Ethyl 8-(4-pentylbiphenyl)-2-phenyl-2-(4-pyrrolidinophenyl)-2-H-naphtho[1,2-b]pyran-5-carboxylate (IIb) was prepared from ethyl 8-bromo-2-phenyl-2-(4-pyrrolidinophenyl)-2-H-naphtho[1,2-b]pyran-5-carboxylate and 4-pentylbiphenylboronic acid in the manner described for Example 1 (m.p. 159° C.; S=0.722).

Example 3

Methyl 8-(4-pentylbiphenyl)-2-phenyl-2-(4-fluorophenyl)-2-H-naphtho[1,2-b]pyran-5-carboxylate (IIc) was prepared from methyl 8-bromo-2-phenyl-2-(4-fluorophenyl)-2-H-naphtho[1,2-b]pyran-5-carboxylate and 4-pentylbiphenylboronic acid in the manner described for Example 1 (m.p. 169-170° C.; S=0.694).

Example 4

Methyl 8-(4-pentylbiphenyl)-2-(4-methoxyphenyl)-2-(4-pyrrolidinophenyl)-2-H-naphtho[1,2-b]pyran-5-carboxylate (IId) was prepared from methyl 8-bromo-2-(4-methoxyphenyl)-2-(4-piperidinophenyl)-2-H-naphtho[1,2-b]pyran-5-carboxylate and 4-pentylbiphenylboronic acid in the manner described for Example 1 (m.p. 89° C.; S=0.629).

Example 5

Methyl 8-(4-pentylbiphenyl)-2-phenyl-2-(4-pyrrolidinophenyl)-2-H-naphtho[1,2-b]pyran-5-carboxylate (IIe) was prepared from methyl 8-bromo-2-phenyl-2-(4-pyrrolidinophenyl)-2-H-naphtho[1,2-b]pyran-5-carboxylate and 4-pentylbiphenylboronic acid in the manner described for Example 1 (m.p. 174° C.; S=0.708).

Example 6

Methyl 8-(4-pentylbiphenyl)-2-phenyl-2-(4-piperidinophenyl)-2-H-naphtho[1,2-b]pyran-5-carboxylate (IIf) was prepared from methyl 8-bromo-2-phenyl-2-(4-piperidinophenyl)-2-H-naphtho[1,2-b]pyran-5-carboxylate and 4-pentylbiphenylboronic acid in the manner described for Example 1 (m.p. 189° C.; S=0.706).

Example 7

Ethyl 8-(4'-[6-(4-pentylphenoxy)hexyloxy]phenyl)-2-phenyl-2-(4-piperidinophenyl)-2-H-naphtho[1,2-b]pyran-5-carboxylate (IIg) was prepared from ethyl 8-bromo-2-phenyl-2-(4-piperidinophenyl)-2-H-naphtho[1,2-b]pyran-5-carboxylate and 4'-[6-(4-pentylphenoxy)hexyloxy]phenylboronic acid in the manner described for Example 1 (m.p. 85-86° C.; S=0.690).

Example 8

Ethyl 8-(4'-[6-(4-pentylphenoxy)hexyloxy]phenyl)-2-(4-fluorophenyl)1-2-(4-methoxyphenyl)-2-H-naphtho[1,2-b]pyran-5-carboxylate (IIh) was prepared from ethyl 8-bromo-2-(4-fluorophenyl)-2-(4-methoxyphenyl)-2-H-naphtho[1,2-b]pyran-5-carboxylate and 4'-[6-(4-pentylphenoxy)hexyloxy]phenylboronic acid in the manner described for Example 1 (m.p. 102° C.; S=0.654).

Example 9

Ethyl 8-(4-pentylbiphenyl)-2-phenyl-2-[4-(4-pentylpiperidino)phenyl]-2-H-naphtho[1,2-b]pyran-5-carboxylate (IIj) was prepared from ethyl 8-bromo-2-phenyl-2-[4-(4-pentylpiperidino)phenyl]-2-H-naphtho[1,2-b]pyran-5-carboxylate and 4-pentylbiphenylboronic acid in the manner described for Example 1 (m.p. 128-129° C., S=0.741).

Example 10

Ethyl 8-(4-[4-(but-3-en-1-yloxy)bezoyloxy]phenyl)-2-(4-piperidinophenyl)-2-phenyl-2-H-naphtho[1,2-b]pyran-5- carboxylate IIj was prepared by the following procedure. Ethyl 8-(4-hydroxyphenyl)-2-(4-piperidinophenyl)-2-phenyl)-2-H-naphtho[1,2-b]pyran-5-carboxylate (obtained from ethyl 8-bromo-2-(4-piperidinophenyl)-2-phenyl)-2-H-naphtho[1,2-b]pyran-5-carboxylate and 4-hydroxyphenylboronic acid in the manner described for Example 1) 0.4 g (0.69 mmol) and 4-(but-3-en-1-yloxy)benzoic acid 0.145 g (0.75 mmol) were dissolved in methylene chloride (30 ml). Dicyclohexyldiimide (DCC) 0.156 g (0.75 mmol) and catalytic amount of dimethylaminopyridine (DMAP) were added. The reaction mixture was stirred at room temperature overnight. The reaction mixture was filtered, the solvent was removed and the residue was flash chromatographed using petroleum ether-ethyl acetate (95-5) on silica gel. Recrystallization from ethyl acetate and hexane gave the title compound (m.p. 100° C.; S=0.703).

Example 11

Methyl 8-(4-[4-cyclohexylbezoyloxy]phenyl)-2-(4-pyrrolidinophenyl)-2-phenyl-2-H-naphtho[1,2-b]pyran-5-carboxylate (IIIk) was prepared from methyl 8-(4-hydroxyphenyl)-2-(4-pyrrolidinophenyl)-2-phenyl)-2-H-naphtho[1,2-b]pyran-5-carboxylate and 4-cyclohexylbenzoic acid in the manner described for Example 10 (m.p. 149° C., S=0.723).

Example 12

Ethyl 8-(4-[4-(4-pentylcyclohexyl)bezoyloxy]phenyl)-2-(4-pyrrolidinophenyl)-2-phenyl-2-H-naphtho[1,2-b]pyran-5-carboxylate (IIIl) was prepared from ethyl 8-(4-hydroxyphenyl)-2-(4-pyrrolidinophenyl)-2-phenyl)-2-H-naphtho[1,2-b]pyran-5-carboxylate and 4-(4-pentylcyclohexyl)benzoic acid in the manner described for Example 10 (m.p. 202-205° C., S=0.731).

Comparative Example 13

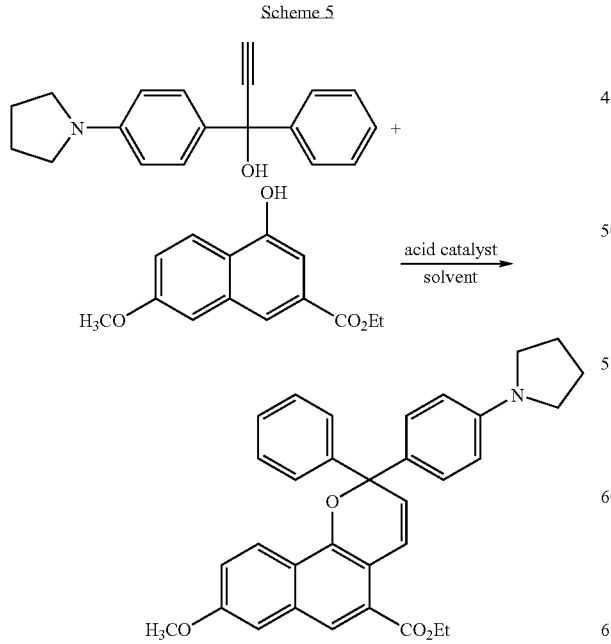

Scheme 5

Ethyl 8-methoxy-2-phenyl-2-(4-pyrrolidinophenyl)-2-H-naphtho[1,2-b]pyran-5-carboxylate was prepared by the following procedure.

1-Phenyl-1-(4-pyrrolidin-1-ylphenyl)prop-2-yn-1-ol 1.35 g (4.87 mmol) and ethyl 4-hydroxy-7-methoxy-2-naphthoate 1.2 g (4.87 mmol) were dissolved in toluene (50 ml) and acidic alumina 3.65 g was added. The reaction mixture was heated at 75° C. for 1 hour. The reaction mixture was filtered and flash chromatographed using toluene on silica gel. Recrystallization from ethyl acetate and hexane gave the title compound (m.p. 191° C.; S=0.430).

The photochromic dye of Comparative Example 13, which does not have a mesogenic group at the C-8 position of the naphthopyran ring, exhibits inferior dichroic properties when incorporated into liquid crystals host material, compared to 2H-naphtho[1,2-b]pyrans having a mesogenic group at C-8 of the naphthopyran ring.

Based on the foregoing, the advantages of the present naphthopyran compounds and optical articles are readily apparent. In certain embodiments, the dichroic-photochromic dyes exhibit good photochromic properties, such as high absorption in the colored state, fast coloring and fading rates, and also are capable of dichroism and light polarization when in a spatially ordered condition, for example when incorporated into liquid crystals or oriented polymer host materials. In certain embodiments, dissolving or dispersing a naphthopyran compound of the present invention into a fluid, mesomorphous, or gel host medium increases the coloration rate and even more drastically the fading rate. In one or more embodiments, the recovery time is reduced.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A naphthopyran compound represented by the formula (I)

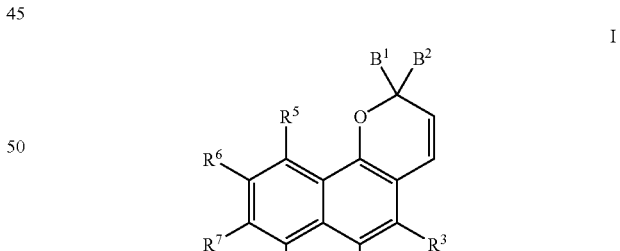

wherein $B^1$ and $B^2$ are selected independently from the group consisting of (i) a phenyl group, (ii) a naphthyl group, (iii) a heterocyclic aromatic group, and (iv) a combination thereof, or wherein $B^1$ and $B^2$ optionally combine to form one or more aromatic rings; wherein $B^1$ and $B^2$ are optionally substituted with one or more substitutents selected from the group consisting of halogen, —$R^a$, —OH, —$OR^a$, —SH, —$SR^a$, —$SOR^a$, —$SO_2R^a$, —$NR^aR^a$, —$NR^bR^c$, —CN, —$NO_2$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$) alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group; wherein $R^3$, $R^4$, $R^5$, $R^6$, and $R^{10}$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein $R^5$ and $R^6$ combine to form a cyclic group, and wherein $R^7$ is a mesogenic group represented by one of the following formulas:

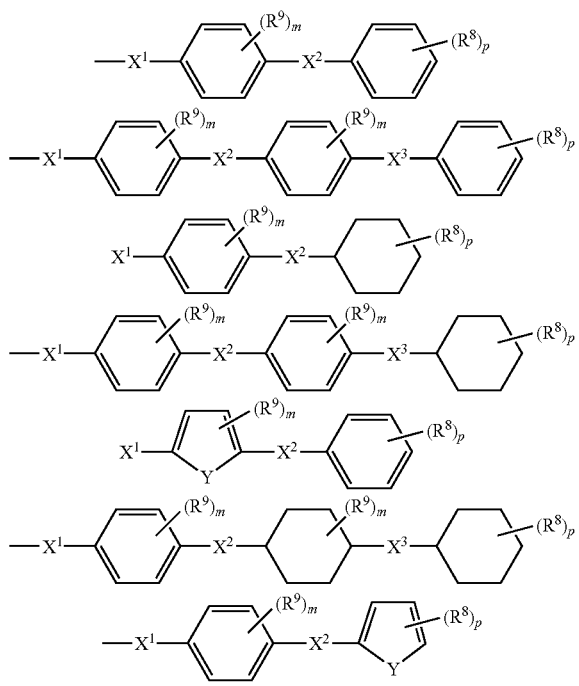

wherein $R^8$ is selected from the group consisting of hydrogen, halogen, —$R^a$, —OH, —$OR^a$, —SH, —$SR^a$, —$NH_2$, —$NR^bR^c$, —CO—$R^a$, —O—CO—$R^a$, and —$CO_2R^a$, wherein $R^9$ is selected from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein an $R^8$ and $R^9$ combine to form a cyclic group, wherein p is an integer from 0 to 5, wherein m is an integer from 0 to 4, wherein $X^1$ is a covalent bond, wherein $X^2$ and $X^3$, identical or different from each other, represent a covalent bond or linking unit selected from the group consisting of an ester, —$R^d$—, —O—, —$OR^d$—, —$OR^dO$—, —$OCOR^d$—, —$OCOR^dO$—, —S—, —CH═CH—, —CH═N—, —C≡C—, and —N═N—, wherein $R^d$ is a linear or branched ($C_{1-18}$) alkyl or a linear or branched ($C_{1-18}$)haloalkyl group, and wherein Y is oxygen, nitrogen, or sulfur.

2. The naphthopyran compound of claim 1, wherein the compound in a UV activated state has an order parameter greater than 0.5.

3. The naphthopyran compound of claim 1, wherein the compound is represented by the formula II

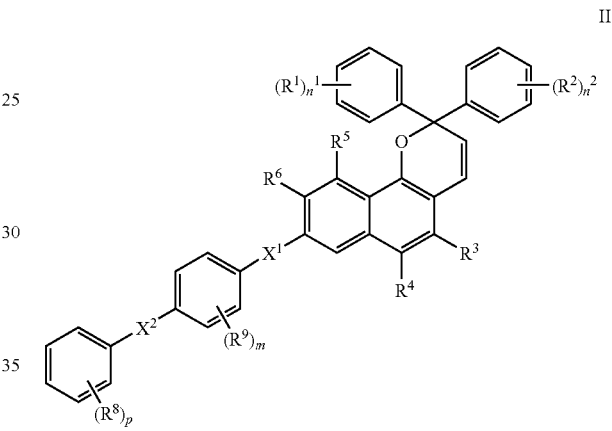

wherein $R^1$, $R^2$, and $R^8$ are selected independently from the group consisting of hydrogen, halogen, —$R^a$, —OH, —$OR^a$, —SH, —$SR^a$, —$NH_2$, —$NR^bR^c$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$)alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group, $n^1$ is an integer from 0 to 5,
$n^2$ is an integer from 0 to 5,
p is an integer from 0 to 5,
m is an integer from 0 to 4,
each $R^3$, $R^4$, $R^5$, $R^6$, and $R^9$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^5$, $R^6$, and $R^9$ combine to form a cyclic group.

4. A naphthopyran compound, wherein said compound is represented by the formula III

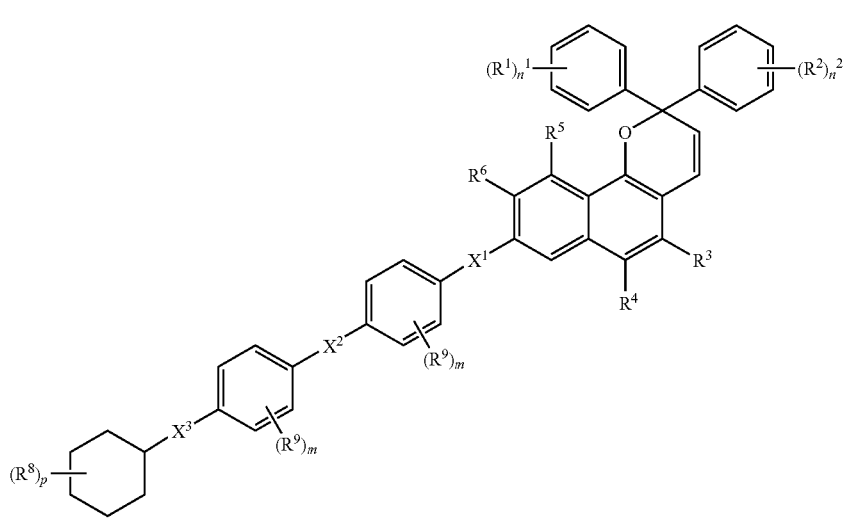

III wherein $R^1$, $R^2$, and $R^8$, are selected independently from the group consisting of hydrogen, halogen, —$R^a$, —OH, —$OR^a$, —SH, —$SR^a$, —$NH_2$, —$NR^bR^c$, —CO—$R^a$, —O—CO—$R^a$, and —$CO_2R^a$, wherein $R^a$ is a linear or branched $(C_{1-20})$ alkyl, $(C_{3-20})$ cycloalkyl, $(C_{4-20})$ polycycloalkyl linear or branched $(C_{1-20})$ alkenyl, linear or branched $(C_{1-20})$ polyalkenyl, linear or branched $(C_{1-20})$ haloalkyl, perhaloalkyl group, linear or branched $(C_{1-20})$ alkynyl, linear or branched $(C_{1-20})$ polyalkynyl, linear or branched $(C_{1-20})$ hydroxyalkynyl, linear or branched $(C_{1-20})$ polyhydroxyalkynyl; $R^b$ and $R^c$ are independently selected from the group consisting of hydrogen and linear or branched $(C_{1-20})$alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group, $n^1$ is an integer from 0 to 5,
$n^2$ is an integer from 0 to 5,
p is an integer from 0 to 5,
m is an integer from 0 to 4,
each $R^3$, $R^4$, $R^5$, $R^6$, and $R^9$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein any two or more of $R^5$, $R^6$, and $R^9$ combine to form a cyclic group, and wherein $X^1$ is a covalent bond, and $X^2$ and $X^3$, identical or different from each other, are covalent bonds or linking units wherein each said linking unit is selected from the group consisting of an ester, —$R^d$—, —O—, —$OR^d$—, —$OR^dO$—, —$OCOR^d$—, —$OCOR^dO$—, —S—, —CH=CH—, —CH=N—, —C≡C—, and —N=N—, wherein $R^d$ is a linear or branched $(C_{1-18})$ alkyl or a linear or branched $(C_{1-18})$haloalkyl group.

5. The naphthopyran compound of claim 4, wherein the compound in a UV activated state has an order parameter greater than 0.5.

6. A naphthopyran compound represented by one of the formulas (a) to (l):

(a)

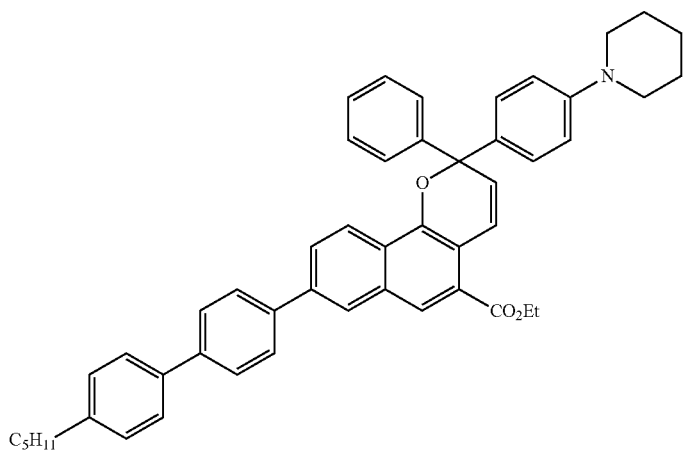

(b)
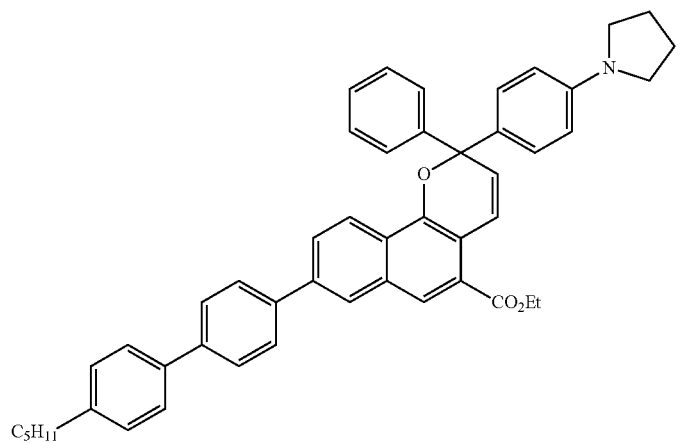
(c)
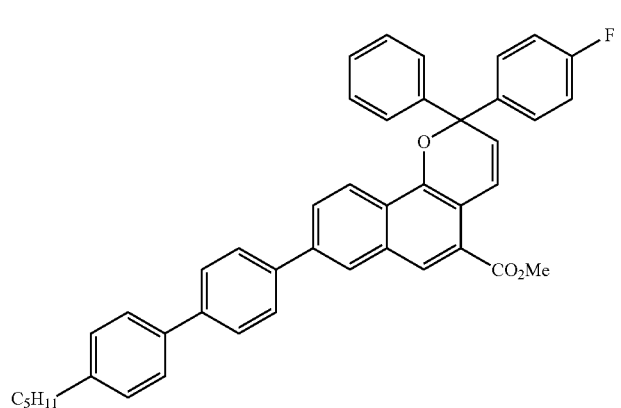
(d)
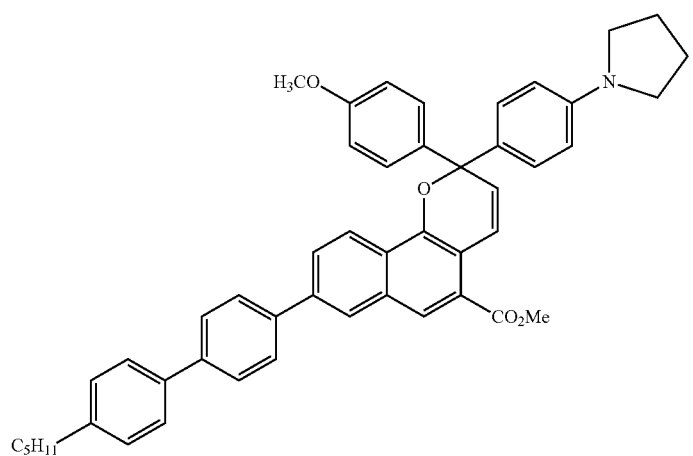

-continued
(e)
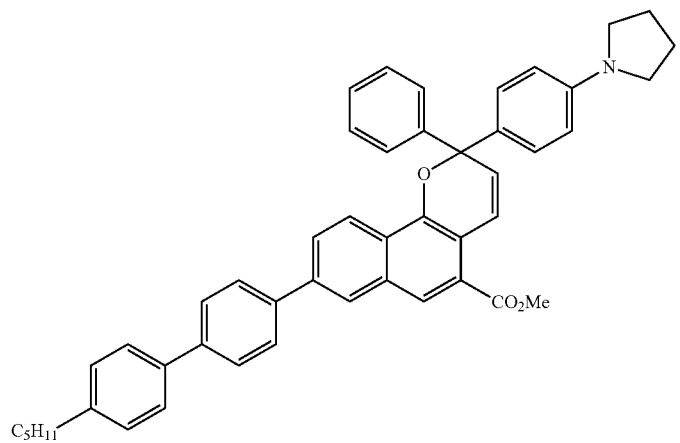
(f)
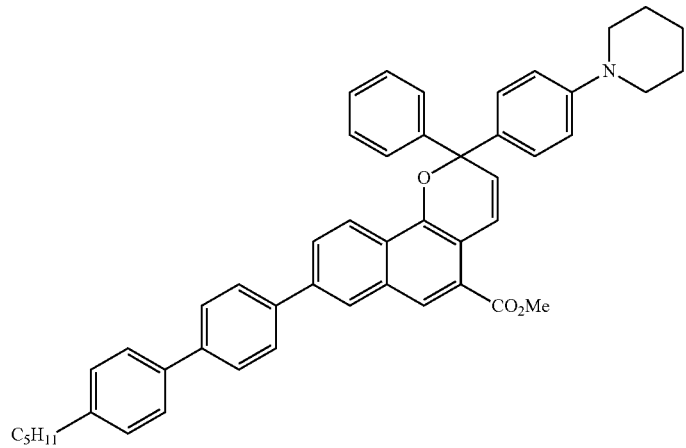
(g)
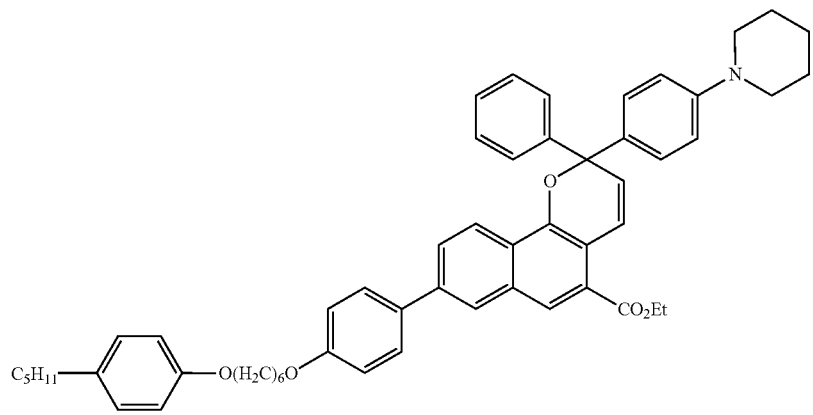

-continued
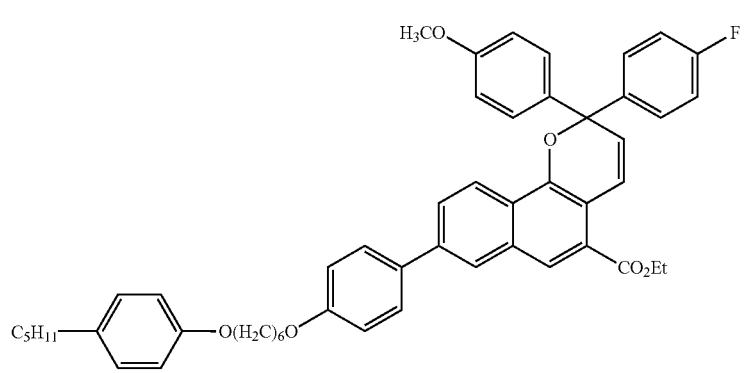
(h)
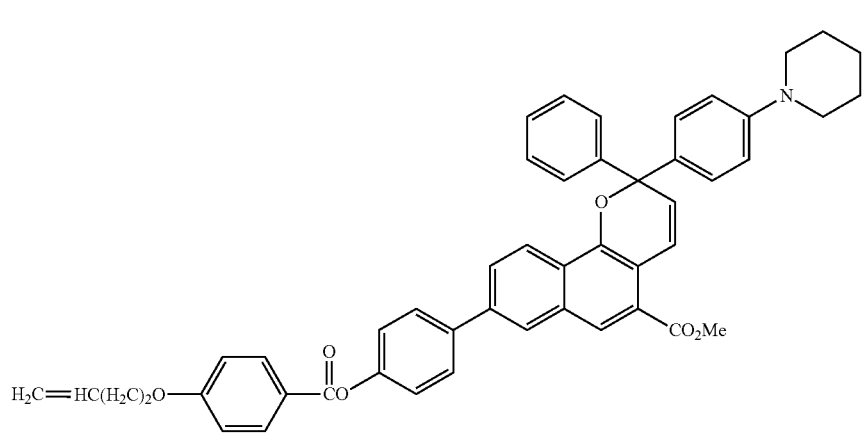
(i)
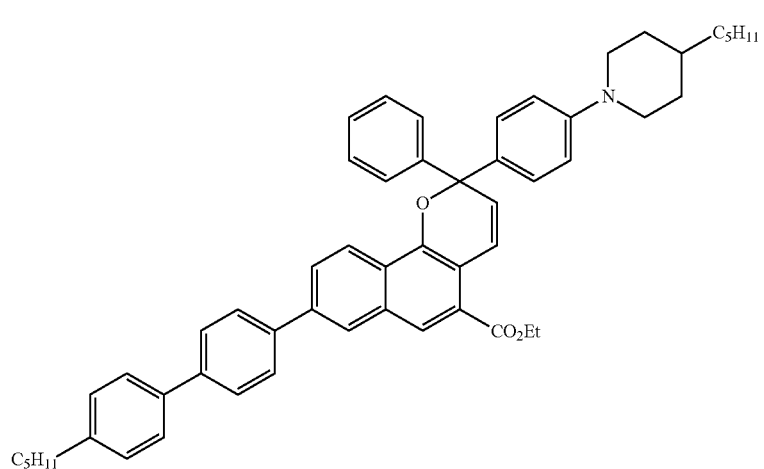
(j)
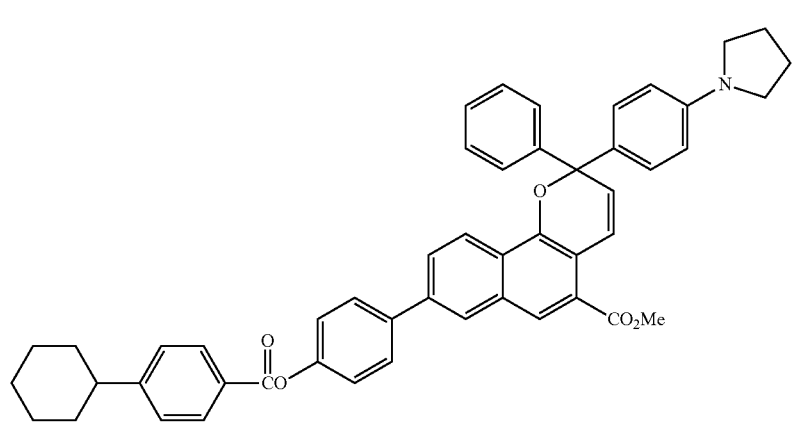
(k)

-continued

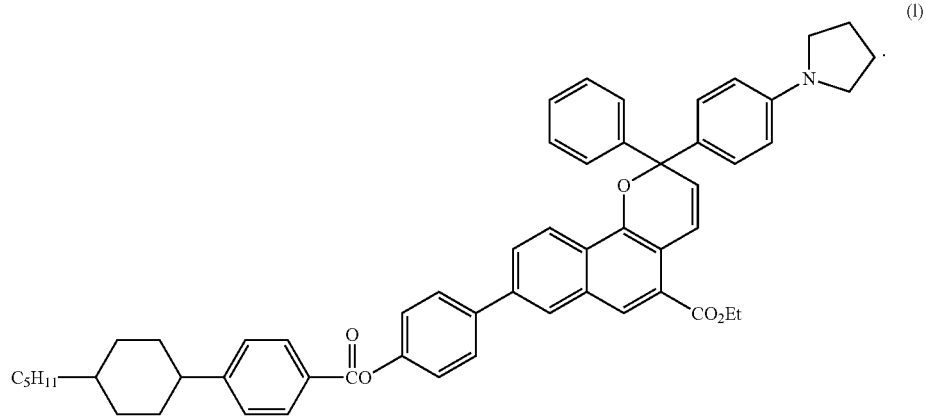
(I)

7. An optical article comprising at least one naphthopyran compound represented by the formula I

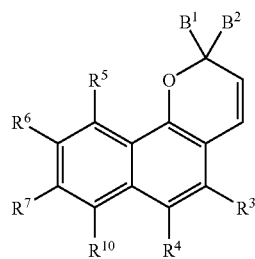
I wherein $B^1$ and $B^2$ are selected independently from the group consisting of (i) a phenyl group, (ii) a naphthyl group, (iii) a heterocyclic aromatic group, and (iv) a combination thereof, or wherein $B^1$ and $B^2$ optionally combine to form one or more aromatic rings; wherein $B^1$ and $B^2$ are optionally substituted with one or more substituents selected from the group consisting of halogen, —$R^a$, —OH, —$OR^a$, —SH, —$SR^a$, —$SOR^a$, —$SO_2R^a$, —$NR^aR^a$, —$NR^bR^c$, —CN, —$NO_2$, —CO—$R^a$, —O—CO—$R^a$, and —$CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$) alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group; wherein $R^3$, $R^4$, $R^5$, $R^6$, and $R^{10}$ are selected independently from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein $R^5$ and $R^6$ combine to form a cyclic group, and wherein $R^7$ is a mesogenic group represented by one of the following formulas:

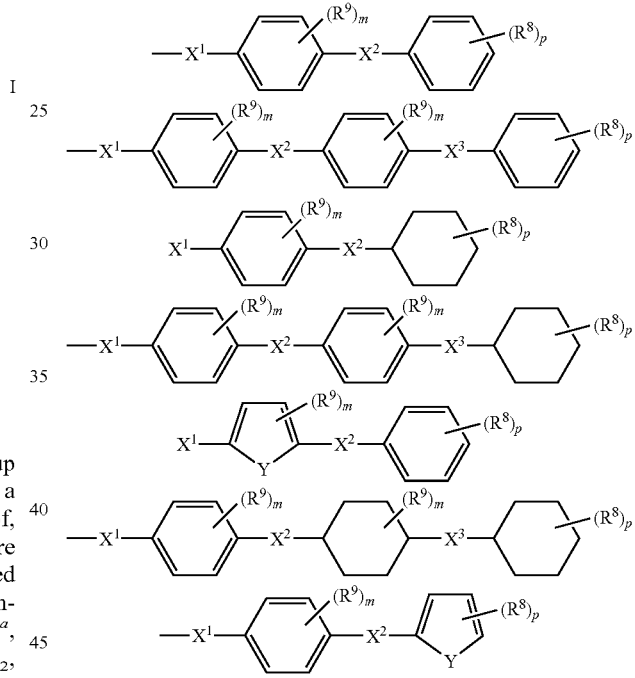

wherein $R^8$ is selected from the group consisting of hydrogen, halogen, —$R^a$, —OH, —$OR^a$, —SH, —$SR^a$, —$NH_2$, —$NR^bR^c$, —CO—$R^a$, —O—CO—$R^a$, and —$CO_2R^a$, wherein $R^9$ is selected from the group consisting of hydrogen, halogen, —$R^a$, —OH, —$OR^a$, —O—CO—$R^a$, —CN, —$NO_2$, —$SO_2R^a$, —$SOR^a$, —SH, —$SR^a$, —$NH_2$, —$NHR^a$, —$NR^aR^a$, and —$NR^bR^c$; or wherein an $R^8$ and $R^9$ combine to form a cyclic group, wherein p is an integer from 0 to 5, wherein m is an integer from 0 to 4, wherein $X^1$ is a covalent bond, wherein $X^2$ and $X^3$, identical or different from each other, represent a covalent bond or linking unit selected from the group consisting of an ester, —$R^d$—, —O—, —$OR^d$—, —$OR^dO$—, —$OCOR^d$—, —$OCOR^dO$—, —S—, —CH═CH—, —CH═N—, —C≡C—, and —N═N—, wherein $R^d$ is a linear or branched ($C_{1-18}$) alkyl or a linear or branched ($C_{1-18}$)haloalkyl group, and wherein Y is oxygen, nitrogen, or sulfur.

8. The optical article of claim 7, wherein the naphthopyran compound is represented by the formula II

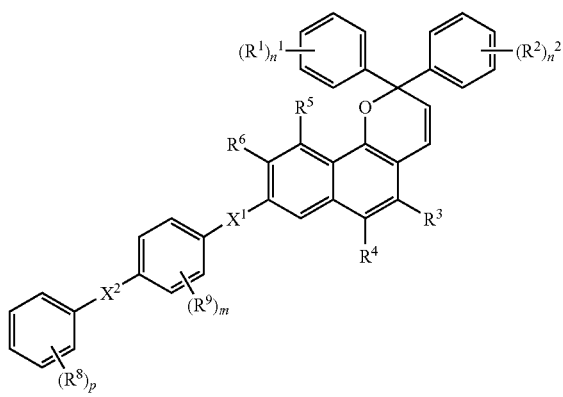

II wherein $R^1$, $R^2$, and $R^8$ are selected independently from the group consisting of hydrogen, halogen, $-R^a$, $-OH$, $-OR^a$, $-SH$, $-SR^a$, $-NH_2$, $-NR^bR^c$, $-CO-R^a$, $-O-CO-R^a$, and $-CO_2R^a$, wherein $R^a$ is a linear or branched ($C_{1-20}$) alkyl, ($C_{3-20}$) cycloalkyl, ($C_{4-20}$) polycycloalkyl linear or branched ($C_{1-20}$) alkenyl, linear or branched ($C_{1-20}$) polyalkenyl, linear or branched ($C_{1-20}$) haloalkyl, perhaloalkyl group, linear or branched ($C_{1-20}$) alkynyl, linear or branched ($C_{1-20}$) polyalkynyl, linear or branched ($C_{1-20}$) hydroxyalkynyl, linear or branched ($C_{1-20}$) polyhydroxyalkynyl; $R^b$ and $R^c$ are independently selected from the group consisting of hydrogen and linear or branched ($C_{1-20}$)alkyl groups, or wherein $R^b$ and $R^c$ combine to form a saturated 5- to 7-member heterocyclic group, or wherein $R^b$ and $R^c$ together and in combination with an adjacent phenyl group form a julolidinyl group, $n^1$ is an integer from 0 to 5,
$n^2$ is an integer from 0 to 5,
p is an integer from 0 to 5,
m is an integer from 0 to 4, each $R^3$, $R^4$, $R^5$, $R^6$, and $R^9$ are selected independently from the group consisting of hydrogen, halogen, $-R^a$, $-OH$, $-OR^a$, $-O-CO-R^a$, $-CN$, $-NO_2$, $-SO_2R^a$, $-SOR^a$, $-SH$, $-SR^a$, $-NH_2$, $-NHR^a$, $-NR^aR^a$, and $-NR^bR^c$; or wherein any two or more of $R^5$, $R^6$, and $R^9$ combine to form a cyclic group.

9. An optical article comprising at least one naphthopyran compound according to claim 4.

10. The optical article according to claim 7, comprising a polymeric host material, and wherein the at least one naphthopyran compound is incorporated into the polymeric host material.

11. The optical article according to claim 10, wherein the polymeric host material comprises a polymer selected from the group consisting of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephtalate), polystyrene, polyfluorostyrene, poly(diethylene glycol bis(alkyl carbonate)) and mixtures thereof.

12. The optical article according to claim 7, further comprising an optical substrate and at least one film or coating, and wherein said film or coating comprises said at least one naphthopyran compound.

13. The optical article according to claim 12, wherein said at least one film or coating includes an anisotropic film or coating comprising an oriented polymer layer and said at least one naphthopyran compound.

14. The optical article according to claim 12, wherein said optical substrate is selected from the group consisting of ophthalmic elements and devices, display elements and devices, windows, mirrors, and lenses.

15. The optical article according to claim 7, wherein the article includes a mixture of a fluid, mesomorphous or gel host medium and said at least one naphthopyran compound, wherein said naphthopyran compound is dissolved or dispersed within the host medium.

16. The optical article according to claim 15, wherein the fluid, mesomorphous, or gel host medium includes an organic solvent, a liquid crystal, a polymer, or mixtures thereof.

17. An optical article comprising at least one naphthopyran compound according to claim 6.

18. The naphthopyran compound of claim 1, wherein the compound in a UV activated state has an order parameter greater than 0.6.

19. The naphthopyran compound of claim 1, wherein the compound in a UV activated state has an order parameter greater than 0.7.

* * * * *